United States Patent [19]

Lifton

[11] Patent Number: 4,657,020

[45] Date of Patent: Apr. 14, 1987

[54] METHOD OF USING A FOREIGN OBJECT PROTECTOR HOOD

[75] Inventor: Lester J. Lifton, Camp Hill, Pa.

[73] Assignee: Jayco Pharmaceuticals, Camp Hill, Pa.

[21] Appl. No.: 753,464

[22] Filed: Jul. 10, 1985

[51] Int. Cl.⁴ .................................................. A61B 17/24
[52] U.S. Cl. ................................................... 128/356
[58] Field of Search .................... 128/328, 348.1, 356, 128/361, 304, 756, 759, 765, 352, 303 R; 604/278–279

[56] References Cited

U.S. PATENT DOCUMENTS

| | | | |
|---|---|---|---|
| 549,904 | 11/1895 | Dunbar | 128/352 |
| 724,913 | 4/1903 | Montgomery | 604/278 |
| 3,472,230 | 11/1969 | Fogarty | 128/304 |
| 3,719,190 | 3/1973 | Avery | 128/785 |
| 4,004,589 | 1/1977 | Neumeier | 604/278 |

FOREIGN PATENT DOCUMENTS 1095457 12/1960 Fed. Rep. of Germany ... 128/348.1
2847633 5/1979 Fed. Rep. of Germany ... 128/303 R Primary Examiner—C. Fred Rosenbaum
Assistant Examiner—Jerome R. Smith, Jr.
Attorney, Agent, or Firm—Millen & White

[57] ABSTRACT

This invention relates to a small bell-shaped latex rubber protector that is designed to be placed over the top of, e.g., an endoscope prior to its passage into a body cavity through a tract thereof. Once it is passed in a folded back position, a sharp, pointed or cutting foreign object can be retrieved from the cavity using a forceps or other accessory. The protector hood is then flipped into the open position by pulling the instrument back through, e.g., the lower esophageal narrowing. The bell-shaped latex protects, for example, the esophagus and posterior pharynx from the foreign body during its removal.

5 Claims, 7 Drawing Figures

METHOD OF USING A FOREIGN OBJECT PROTECTOR HOOD

BACKGROUND OF THE INVENTION

This invention relates to a device for use in removal of foreign objects from a tract of the human body such as the gastrointestinal tract.

It is often the case that foreign objects will enter the human body through regions such as the gastrointestinal tract, for example, by swallowing. Typically, when it is desired to remove a foreign object through the tract of the human body, often damage is caused by removal of the object. Up to now no device has been designed for use, for example, with an endoscope or other like device for removing such objects.

One prior art device which at first glance appears similar in structure, but fails to provide the necessary function is disclosed in U.S. Pat. No. 3,719,190. This patent discloses a heart stimulation eletrode with a conical positioning parachute. The structure of the parachute responds to the blood flowing in a vein to draw the electrode into the heart. When the electrode is withdrawn from the heart the parachute inverts allowing for withdrawal of the electrode without damage to the vein tissue. However, this patent fails to disclose a device for permitting withdrawal of a foreign body from the human cavity and instead, the functioning of the parachute is merely for the purpose of preventing damage caused by the parachute itself. There is no means provided for covering the electrode upon withdrawal through the vein.

Also related is the device disclosed in U.S. Pat. No. 724,913 which relates to a syringe nozzle suitable for irrigating, for example, the rectum. The syringe nozzle includes a bell-shaped member secured to the tip of the syringe with the bell-shaped member sealing against the which the syringe is being employed. This device merely provides a sealing function and the problems of removing a foreign object, with a device which inverts to provide a protective function, from the human cavity through a passage thereof is not addressed.

SUMMARY OF THE INVENTION

It is thus an object of the present invention to provide a device for facilitating removal of foreign objects from cavities and through tracts in the human body while preventing damage to the passage tract or cavity of the human body caused by the foreign object upon removal.

It is another object of the present invention to provide such a device for use in combination with an endoscope and instruments for facilitating grasping and removal of the foreign objects from the human cavity. Upon further study of the specification and appended claims, further objects and advantages of this invention will become apparent to those skilled in the art.

In accordance with the invention a device is provided for protecting an internal tract of a human body during removal of a foreign object therethrough. The device comprises protecting means which is movable between a first-position to permit passage thereof into and through the tract of the human body to the region wherein a foreign object is located, and a second position for covering the foreign object when being removed for preventing contact between the foreign object and the walls of the tract of the human body. In addition, attachment means is provided for attaching the protecting means to an instrument to be passed through the human tract to retrieve the foreign object.

In a more specific aspect, the invention is directed to a protecting means sized for passage through a relatively large human body tract such as the gastrointestinal tract. The attachment means is adapted for attaching the protecting means to an endoscope and/or forceps or other like retrieving devices used to retrieve the foreign objects from the human cavity. In a preferred embodiment, the device is a latex hood which is sufficiently flexible to be passed in a folded back position through the gastrointestinal tract to the location of a sharp pointed or cutting foreign body. The protector hood, once the foreign object is grasped by forceps or other accessory is then automatically flipped into the open position by pulling the instrument back through the lower esophageal narrowing. The bell-shaped latex protects the esophagus and posterior pharynx from the foreign body during its removal.

When used with an endoscope, the device provides advantages by flipping back during insertion to permit full visualization. The narrowing at the junction of the esophagus and stomach are then used to cause automatic straightening out of the bell-shaped hood. In addition, the narrow end of the hood is such that it easily attaches to the endoscope by stretching over the end and then securing it in place. A rubber band can also be used to additionally secure it in place.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein.

DETAILED DISCUSSION OF THE INVENTION

Figure 1:
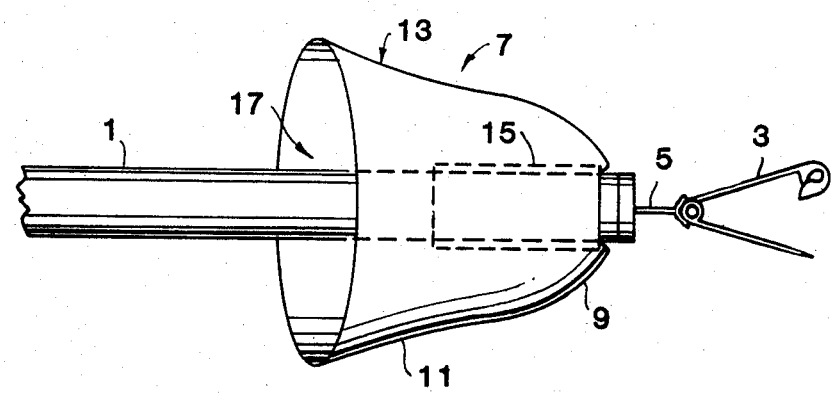
FIG. 1 is schematic diagram showing the device of the invention as mounted, for example, retracted or folded back position on a device such as an endoscope after having grasped an object in the human body cavity.

As shown in FIG. 1, the device of the invention is shown in a retracted position after having been inserted through the tract of a human body with a foreign object attached to the instrument, for example, a probe such as an endoscope 1, for being retrieved from the human body cavity. As shown in FIG. 1, the device of the invention 7 which is a foreign object protective hood 7 would generally be attached at a tubular flexible extension 15 to the endoscope 1. It includes a generally bell-shaped section 13 which opens into a wide mouth area 17 having a peripheral edge which engages the wall of the track so that when being retracted it folds back into a protective position by bending at a generally more flexible region 9 of the bell-shaped portion 13 with the wide expanding portion of the bell-shaped portion 13 being a thicker region 11. In this embodiment, the endoscope is shown with a magnetic attaching means 5 which is used to secure a pin 3, for example, which has been swallowed by a child.

Figure 2:
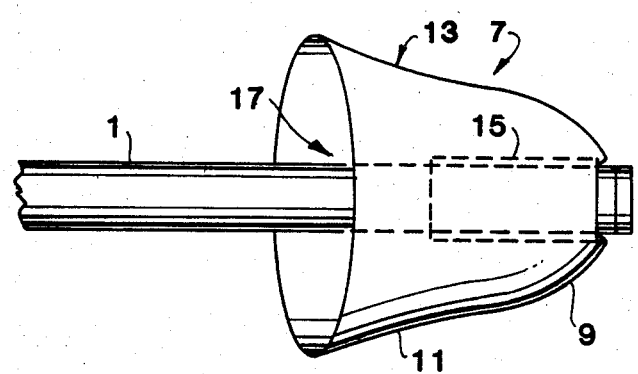
FIG. 2 is a schematic diagram of the device of the invention in retracted or folded back position attached to an endoscope and ready for insertion through a tract of the human body.

The figure of FIG. 2 shows the device 7 attached to the endoscope 1 in position for being passed through the tract of the human body just prior to entering the cavity region wherein the object to be retrieved is located in much the same manner as shown in FIG. 1.

Figure 3:
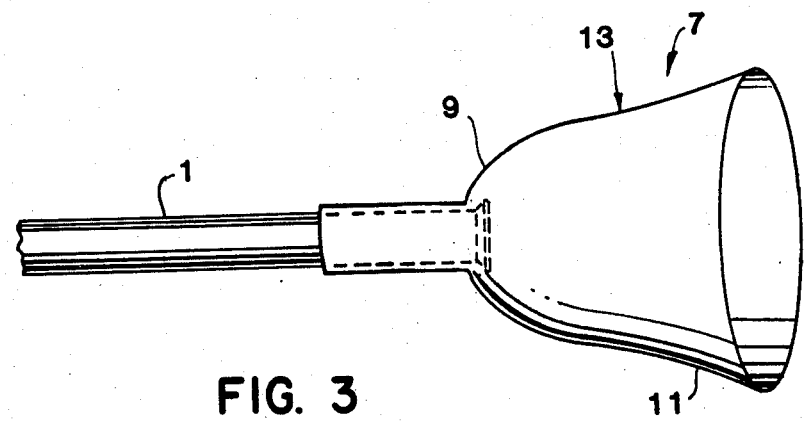
FIG. 3 is a view showing the device of the invention after having been folded back into the open position for protecting the walls of the human body tract from damage by the grasped object.

As shown in FIG. 3, the device of the invention is shown in a protective position. The inversion of the hood 13 was caused typically by contact with the walls of the tract of the human body upon withdrawal, and preferably a narrowing of the walls which is sufficient to exert enough force upon retraction on the more flexible region 9 of the bell-shaped portion 13 to cause it to invert upon retraction of the device by means of retracting the endoscope 1 with the foreign object to be removed firmly protected and secured within the hood portion 13.

Figure 4B:
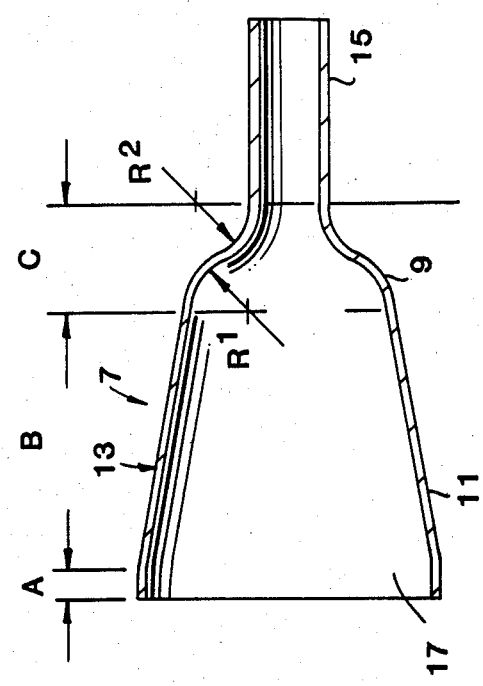
FIGS. 4a and 4b respectively show a view from the open end of the device of the invention and a cross-sectional view of the device of the invention showing the structural details thereof.
Figure 4A:
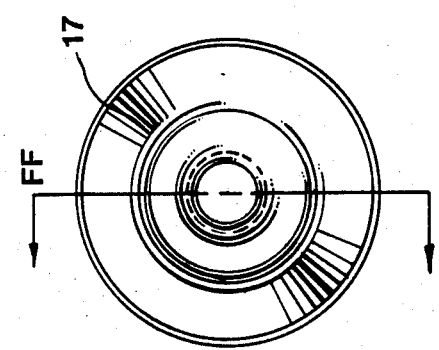

As shown in FIG. 4a, the wide open mouth 17 of the device tapers into a connecting portion 15 for attachment to for example, an endoscope 1. Other uses can be as an atachment to forceps or other like devices for retrieving foreign objects from the body.

FIG. 4b shows a cross section view along the side along lines FF of FIG. 4a showing the various detailed features of the invention. As shown therein, there is a connecting portion 15 which has a wall thickness of sufficient rigidity to be securely attached by frictional engagement to a device such as an endoscope for passage of the protecting hood into the body cavity. However, the wall thickness of connecting portion 15 must also be of sufficient flexibility to permit stretching thereof for passage over the end of the endoscope 1 to be attached thereto. A region 9 having internal radius of curvature R' combined with external radius of curvature $R^2$ generally shown by a region designated as C is provided which is of reduced thickness to permit flexibility in flipping the protecting hood from one position to the other. The selection of the wall thickness and flexibility is well known to one of ordinary skill in the art once the body cavity within which the protective hood is to be used is known.

For example, a body cavity connected by a tract which does not substantially reduce its diameter would require a region C of greater flexibility and thus thinner wall thickness which would move from one position to the other with little or no force depending on the movement of the endoscope in the tract of the body and with minimal wall engagement. On the other hand, a tract which decreases in diameter on withdrawal would not require such a reduced wall thickness as compared to the rest of the device since the frictional engagement with the walls upon retraction could be employed to generate sufficient force to cause the inverting from one position to the other of the protective hood. Region B of the protective hood 7 hood portion 13 generally flares outwardly expanding toward the wide mouth 17 and terminating in a region A which generally tapers into parallel extension with the portion 15 used to connect to the endoscope.

As noted, the device can be made of latex or other flexible material with latex being the preferred material. The material employed must be such that the hood is sterilizable since it is to be used within the body to prevent the risk of infection. To this end, the materials which can be employed are conventional and would be well known to those of ordinary skill in the art.

Included among these materials are such as silicone rubber, shaped by an injection molding techique. More particularly, any material that is bio-compatible, flexible and elastic would be suitable.

In addition to the above discussed embodiment, the hood can be made of a size such as to fit into a catheter small enough to fit through the accessory channel of an endoscope. In this case the hood will be positioned over, e.g., a grasping type forceps or other instrument, to grasp a foreign body. By withdrawing the hood into the catheter, this will cause it to fold onto itself.

In actual use, once the catheter is passed through the endoscope, it is withdrawn, allowing the hood to expand to provide protection against the foreign body. In this case the hood will not flip into a protecting position since it will already be in the protecting position. Instead, it will be sufficiently flexible to be collapsible so as to be in a collapsed position when located in the catheter. When the catheter is withdrawn, it expands to provide the protection desired. This embodiment will look very much like that of FIGS. 3, 4a and 4b, except that it will not flip back as shown in FIGS. 1 and 2.

Figure 5:
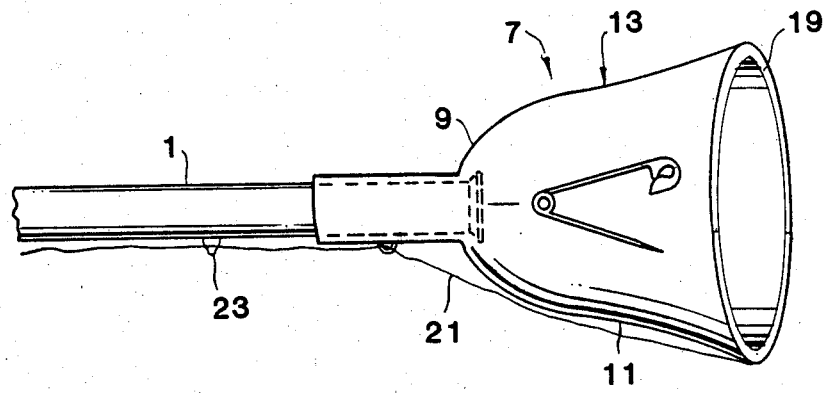
FIGS. 5 and 6 illustrate another embodiment of the invention showing actuation with a drawstring.
Figure 6:
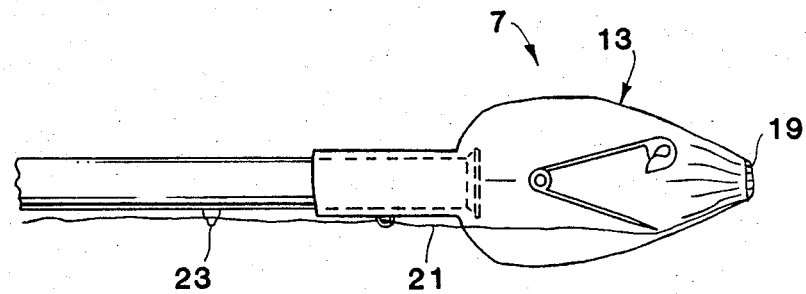

A still further embodiment is shown in FIGS. 5 and 6 involves the use of a drawstring arrangement. As shown in FIG. 5 the arrangement includes a channel 19 at the open end of the hood 7. A drawstring 21 extends through the channel 19, and backward along the endoscope 1 and is held in proximity thereto by string support means 23. The string support means are shaped as blunt as possible to avoid injury to the body cavity in which it is employed.

As shown in FIG. 5, when the foreign object is safely contained within the hood 7, the string 21 is pulled to close the open end of the hood 7 into a sacklike configuration.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of removing a foreign object from an internal track of a body, such as a human body, without damaging the wall defining the track, the method comprising the steps of:
   inserting a probe into the track in a first direction with an inverted bell-shaped, flexible shield fixed thereto, the bell-shaped shield having an opening facing opposite the first direction and having a peripheral edge engaging the wall of the track;
   grasping the object with a tool extending from the probe;
   inverting the bell-shaped shield to cover the now grasped object by moving the probe in a second longitudinal direction opposite the first direction with the peripheral edge of the shield in engagement with the wall of the track, and
   removing the object from the track while preventing engagement of the object therewith by continuing longitudinal motion of the probe in the second direction.

2. The method of claim 1 further including the step of constricting the edge of the shield to completely enclose the foreign object within the shield.

3. A method of removing a foreign object from an internal track of a body, such as a human body, by using an endoscope, catheter, grasping tool and flexible shield, the method comprising the steps of:

folding the flexible shield, which is bell-shaped with a free edge when expanded, into the catheter and over the grasping tool with the free edge thereof facing in a first direction;

inserting the catheter with the flexible shield folded therein in to an accessory channel within the endoscope;

inserting the endoscope through the body track and into proximity with the foreign object;

removing the catheter to expand the flexible shield;

grasping the foreign body with the grasping tool;

enveloping the foreign body within the bell-shaped shield; and withdrawing the endoscope from the track along with the shield enveloping the foreign body to remove the foreign body from the track while preventing the foreign body from engaging the track during withdrawal.

4. The method of claim 3 further including the step of constricting the free edge of the shield after enveloping the object to completely enclose the object within the shield.

5. The method of claim 14 wherein the step of constricting the free edge of the shield comprises pulling a draw string disposed around the free edge to substantially close the free edge.

* * * * *